United States Patent [19]
Beshel

[11] Patent Number: 5,836,934
[45] Date of Patent: Nov. 17, 1998

[54] CLOSED SYSTEM AND METHODS FOR MIXING ADDITIVE SOLUTIONS WHILE REMOVING UNDESIRED MATTER FROM BLOOD CELLS

[75] Inventor: Richard Beshel, McHenry, Ill.

[73] Assignee: Baxter International Inc., Deerfield, Ill.

[21] Appl. No.: 479,911

[22] Filed: Jun. 7, 1995

[51] Int. Cl.[6] .................................................. A61B 19/00
[52] U.S. Cl. ............................ 604/410; 210/231; 210/782
[58] Field of Search ............................. 604/406, 410, 604/4, 5; 210/436, 782, 645, 231

[56] References Cited

U.S. PATENT DOCUMENTS

| | | |
|---|---|---|
| 4,350,585 | 9/1982 | Johansson et al. . |
| 4,396,382 | 8/1983 | Goldhaber . |
| 4,608,178 | 8/1986 | Johansson et al. . |
| 4,767,541 | 8/1988 | Wisdom . |
| 4,804,363 | 2/1989 | Valeri .......................................... 604/6 |
| 4,807,676 | 2/1989 | Cerny et al. ................................. 604/6 |
| 4,810,378 | 3/1989 | Carmen et al. . |
| 4,985,153 | 1/1991 | Kuroda et al. ........................... 604/410 |
| 4,997,577 | 3/1991 | Stewart . |
| 5,061,451 | 10/1991 | Gänshirt et al. . |
| 5,092,996 | 3/1992 | Spielberg ................................. 604/406 |
| 5,128,048 | 7/1992 | Stewart et al. . |
| 5,152,905 | 10/1992 | Pall et al. ................................. 604/406 |
| 5,180,504 | 1/1993 | Johnson et al. .......................... 604/406 |
| 5,269,946 | 12/1993 | Goldhaber et al. ...................... 604/406 |
| 5,456,845 | 10/1995 | Nishimura et al. ...................... 604/406 |
| 5,527,472 | 6/1996 | Bellotti et al. . |

*Primary Examiner*—John G. Weiss
*Assistant Examiner*—Ki Yong O
*Attorney, Agent, or Firm*—Daniel D. Ryan; Denise M. Serewicz; Bradford R. L. Price

[57] ABSTRACT

A blood processing system and associated method include a first variable volume chamber to hold blood and a second variable volume chamber to hold additive solution for blood. The system and method further employ a separation device to remove undesired material from blood. An actuated element exerts external force simultaneously upon both first and second variable volume chambers to expel a first flow of blood from the first variable volume chamber and a second flow of additive solution from the second variable volume chamber. The system and method mix outside the first and second variable volume chambers the blood flow with the flow of additive solution to create a mixed flow comprising blood and additive solution. The system and method direct the mixed flow of blood and additive solution through a filter to remove undesired matter from the blood.

6 Claims, 5 Drawing Sheets

CLOSED SYSTEM AND METHODS FOR MIXING ADDITIVE SOLUTIONS WHILE REMOVING UNDESIRED MATTER FROM BLOOD CELLS

FIELD OF THE INVENTION

The invention generally relates to blood collection and processing systems and methods. In a more particular sense, the invention relates to systems and methods for removing leukocytes from red blood cells prior to transfusion or long term storage.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Systems composed of multiple, interconnected plastic bags have met widespread use and acceptance in the collection, processing and storage of these blood components. In the United States, these multiple blood bag systems are subject to regulation by the government. For example, the plastic materials from which the bags and tubing are made must be approved by the government. In addition, the maximum storage periods for the blood components collected in these systems are prescribed by regulation.

In the United States, whole blood components collected in a nonsterile, or "open", system (i.e. one that is open to communication with the atmosphere) must, under governmental regulations, be transfused within twenty-four hours. However, when whole blood components are collected in a sterile, or "closed", system (i.e., one that is closed to communication with the atmosphere), the red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

In collecting whole blood components for transfusion, it is desirable to minimize the presence of impurities or other materials that may cause undesired side effects in the recipient. For example, because of possible febrile reactions, it is generally considered desirable to transfuse red blood cells substantially free of the white blood cell components, particularly for recipients who undergo frequent transfusions.

One way to remove white blood cell components is by washing the red blood cells with saline. This technique is time consuming and inefficient, as it can reduce the number of red blood cells available for transfusion. The washing process also exposes the red blood cells to communication with the atmosphere, and thereby constitutes a "non-sterile" entry into the storage system. Once a non-sterile entry is made in a previously closed system, the system is considered "opened", and transfusion must occur within twenty-four hours, regardless of the manner in which the blood was collected and processed in the first place. In the United States, an entry into a blood collection system that presents the probability of non-sterility that exceeds one in a million is generally considered to constitute a "non-sterile" entry.

Another way to remove white blood cell components is by filtration. Systems and methods for accomplishing this within the context of conventional multiple blood bag configurations are described in Wisdom U.S. Pat. Nos. 4,596,657 and 4,767,541, as well as in Carmen et al U.S. Pat. Nos. 4,810,378 and 4,855,063. In these arrangements, an in line leukocyte filtration device is used. The filtration can thereby be accomplished in a closed system. However, the filtration processes associated with these arrangements require the extra step of wetting the filtration device before use with a red blood cell additive solution or the like. This added step complicates the filtration process and increases the processing time.

Other systems and methods for removing white blood cell components in the context of closed, multiple blood bag configurations are described in Stewart U.S. Pat. No. 4,997,577 and Stewart et al. U.S. Pat. No. 5,128,048. In these filtration systems and methods, a transfer assembly dedicated solely to the removal of leukocytes from red blood cells is used. The transfer assembly also has a second fluid path that bypasses the separation device for the purpose of transporting liquid and air around the separation device.

A need still exists for further improved systems and methods for removing undesired matter from blood components prior to transfusion or storage in a way that lends itself to use in closed multiple blood bag system environments.

SUMMARY OF THE INVENTION

The invention provides a multiple container blood collection system for conveniently processing the various components of blood.

The systems and methods that embody the features of the invention are particularly well suited for use in association with closed blood collection systems and conventional sterile connection techniques, thereby permitting separation to occur in a sterile, closed environment.

One aspect of the invention provides a blood processing system and associated method that include a first variable volume chamber to hold blood and a second variable volume chamber to hold additive solution for blood. The system and method further employ a separation device to remove undesired material from blood.

According to this aspect of the invention, an actuated element exerts external force simultaneously upon both first and second variable volume chambers. The force simultaneously expels a first flow of blood from the first variable volume chamber and a second flow of additive solution from the second variable volume chamber.

The system and method that incorporate this aspect of the invention also include a fluid flow system to convey fluid flow in response to the external force exerted by the actuated element and without the application of any additional external pumping force. The fluid flow system includes a first branch communicating with the first variable volume chamber to convey the first flow of blood, a second branch communicating with the second variable volume chamber to convey the second flow of additive solution simultaneously with and independent of the first flow, and a third branch communicating with the first and second branches to mix outside the first and second variable volume chambers the blood in the first branch with the additive solution in the second branch to create a mixed flow comprising blood and additive solution. The third branch further communicates with the filter to direct the mixed flow of blood and additive solution through the filter to remove undesired matter from the blood.

In a preferred embodiment, the third branch also communicates with a transfer chamber to direct the mixed flow of blood and additive solution from the filter into the transfer chamber.

In one embodiment, the first and second variable volume chambers comprise, respectively, a first flexible container and a separate second flexible container. In an alternative embodiment, the first and second variable volume chambers comprise compartments within a single flexible container.

While the systems and methods that embody the features of the invention can be used to process all types of blood components, they are well suited for the removal of white blood cell components from red blood cells by filtration prior to transfusion or long term storage. Therefore, in a preferred embodiment, the separation device removes leukocytes by filtration.

According to another aspect of the invention, the first variable volume chamber includes spaced apart first and second ports.

According to this aspect of the invention, as the actuated element exerts external force simultaneously upon both first and second variable volume chambers, the force simultaneously expels the first flow of red blood cells from the first port of the first variable volume chamber, the second flow of additive solution for the red blood cells from the second variable volume chamber, as well as a third flow of plasma constituent from the second port of the first variable volume chamber. This arrangement can be used to keep a substantial population of leukocytes contained within the first variable volume chamber, resulting in both red blood cells and plasma constituent that are depleted of leukocytes. The separation device further enhances the removal of additional leukocytes from the red blood cells by filtration, while simultaneously mixing the red blood cell flow with the second flow of additive solution.

Other features and advantages of the invention will become apparent upon review of the following description, drawings, and appended claims.

DESCRIPTION OF THE PREFERRED EMBODIMENTS

Figure 1:
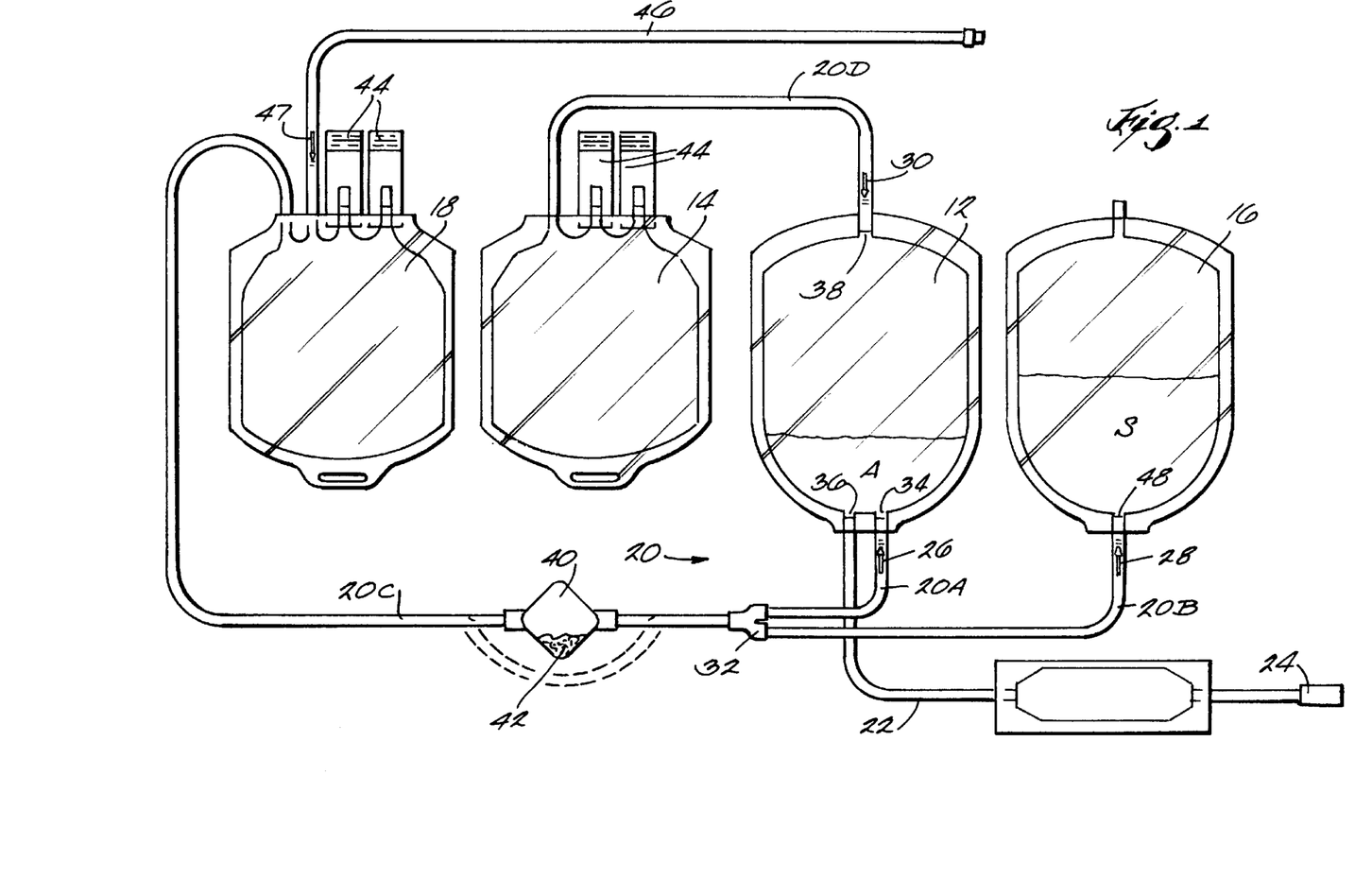
FIG. 1 is a schematic view of a blood collection assembly that embodies the features of the invention.

A blood collection assembly 10 is shown in FIG. 1. In the illustrated embodiment, the assembly 10 serves to separate and store the red blood cells as well as the plasma and platelet blood components by conventional centrifugation techniques. The assembly 10 also serves to simultaneously mix additive solution to and remove undesired matter from the red blood cells before storage. In the illustrated embodiment, the undesired matter comprises leukocytes, which are removed by filtration.

As used herein, the term "filtration" is intended to include separation achieved by various centrifugal and non-centrifugal techniques, and not merely "filtration" in the technical sense. Separation can occur by absorption, columns, chemical, electrical, and electromagnetic means. The term "filtration" is thus broadly used in this specification to encompass all of these separation techniques as well.

In the illustrated and preferred embodiment shown in FIG. 1, the assembly 10 includes a primary bag or container 12, an auxiliary bag or container 16 containing an additive solution S, and two transfer bags or containers 14 and 18. The primary bag 12 includes an integrally attached donor tube 22 that carries a phlebotomy needle 24.

In the illustrated and preferred embodiment, the primary bag 12 has a top and bottom port configuration like that described and claimed in Johansson et al U.S. Pat. No. 4,608,178. A commercial embodiment of such a system is sold by Baxter Healthcare Corporation (Fenwal Division) under tradename OPTI-SYSTEM. It should be appreciated that, alternatively, all the ports associated with the primary bag can be arranged along the top of the bag, as is also conventional for blood bags.

Branched tubing 20 integrally attaches the primary bag 12 to the bags 14, 16, and 18. The tubing 20 is divided into tube branches 20A; 20B; 20C; and 20D.

In the particular configuration shown in FIG. 1, the bag 12 includes two bottom ports 34 and 36 and a top port 38. The donor tube 22 communicates with the bottom port 36 for conveying whole blood from a donor into the primary bag 12. The primary bag 12 contains a suitable anticoagulant A for this reason. The branch tube 20A communicates with the bottom port 34. The branch tube 20A joins the branch tube 20C through a conventional "Y" or "T" connector 32. The branch tubes 20A and 20C serve together to convey fluid from the bottom region of the bag 12 into the transfer bag 18. In use, the transfer bag 18 is intended to receive the red blood cell component of the whole blood collected in the primary bag 12. The transfer bag 18 ultimately serves as the storage container for the red blood cell component.

The branch tube 20D communicates with the top port 38 of the bag 12, which serves to convey fluid from the top region of the bag 12 into the transfer bag 14. In use, the transfer bag 14 is intended to receive the plasma blood component of the whole blood collected in the primary bag 12 through branch tube 20D. The transfer bag 14 ultimately serves as the storage container for the plasma blood component.

Depending upon the particular objectives of the blood processing procedure, the plasma component can carry substantially all the platelets associated with the collected whole blood, in which case the component would be called "platelet-rich plasma" or PRP. Alternatively, the plasma component can be substantially free of platelets, in which case the component would be called "platelet-poor plasma" or PPP.

The branch tube 20B communicates through a bottom port 48 with the additive solution bag 16. The branch tube 20B thereby serves to convey additive solution from the bag 16.

In the illustrated embodiment, the transfer bag 16 contains a storage solution S for the red blood cell (RBC) component of the whole blood collected in the primary bag 12. One such solution is disclosed in Grode et al U.S. Pat. No. 4,267,269. Another such solution is conventionally called "SAG-M" solution.

The connector 32 joins branch tubes 20A, 20B, and 20C. The branch tube 20C thereby also serves to mix RBC from bag 12 with additive solution from bag 16 during conveyance into the transfer bag 18.

The branch tube 20C further includes an in line filter 40 for separating leukocytes from RBC-additive solution mixture being conveyed into the transfer bag 18. In use, the transfer bag 18 receives the RBC component mixed with the storage solution S after passage through the filter 40.

In this arrangement, the filter 40 contains a conventional fibrous filtration medium 42 suited for the removal of leukocytes from red blood cells. The filtration medium 42 can include cotton wool, cellulose acetate or another synthetic fiber like polyester. It should be appreciated that the filter 40 can be used to remove other types of undesired materials from the RBC component, depending upon its particular construction.

In the illustrated embodiment, the assembly 10 includes in line fluid flow control devices 26; 28; and 30 in the tube branches 20A; 20B; and 20D, respectively. In the illustrated arrangement, the flow control devices 26; 28; and 30 take the form of conventional frangible cannulas. Each cannula normally blocks fluid flow through its associated tube branch. When manually bent, the cannula breaks apart to open the associated tube branch.

In the illustrated embodiment, the cannula 26 controls fluid flow through the branch tube 20A. The cannula 28 controls fluid flow through the branch tube 20B. The cannula 30 controls fluid flow through the branch tube 20D.

In the illustrated embodiment, the transfer bags 14 and 18 include normally sealed administration ports 44. The ports 44 are enclosed within conventional tear-away flaps. When opened, the flaps expose the ports 44 for attachment to conventional transfusion or transfer tubing (not shown). In the illustrated embodiment, the transfer bag 18 also includes a length of transfusion tubing 46 integrally connected to it, along with an in line cannula 47.

The bags and tubing associated with the processing assembly 10 can be made from conventional approved medical grade plastic materials, such as polyvinyl chloride plasticized with di-2-ethylhexyl-phthalate (DEHP).

The assembly 10 shown in FIG. 1, once sterilized, constitutes a sterile, "closed" system, as judged by the applicable standards in the United States. The assembly 10 remains "closed" during processing. This assures that the longest authorized storage intervals can be used for the components collected.

It should be appreciated that, alternatively, the assembly 10 can initially comprise a group of sterile subassemblies. For example, the primary bag 12 could comprise one sterile subassembly, the transfer bag 14 another sterile subassembly, the transfer bag 18 and filter 40 yet another sterile subassembly, and the additive solution bag 16 still another sterile subassembly. In this arrangement (not shown), the branch tubes 20A, 20B, 20C, and 20D would carry mating sterile connection devices that the user connects together at time of use, thereby creating the single integral assembly 10 shown in the drawings. Sterile connection devices that could be used for this purpose are shown in Granzow et al. U.S. Pat. Nos. 4,157,723 and 4,265,280. In another alternative arrangement, sterile subassemblies can be assembled together by other means and then undergo terminal sterilization after assembled.

In use, the primary bag 12 receives whole blood from a donor through the donor tubing 22. Afterward, the donor tubing 22 is preferably sealed and disconnected from the primary bag 12 using conventional techniques.

Figures 2, 3:
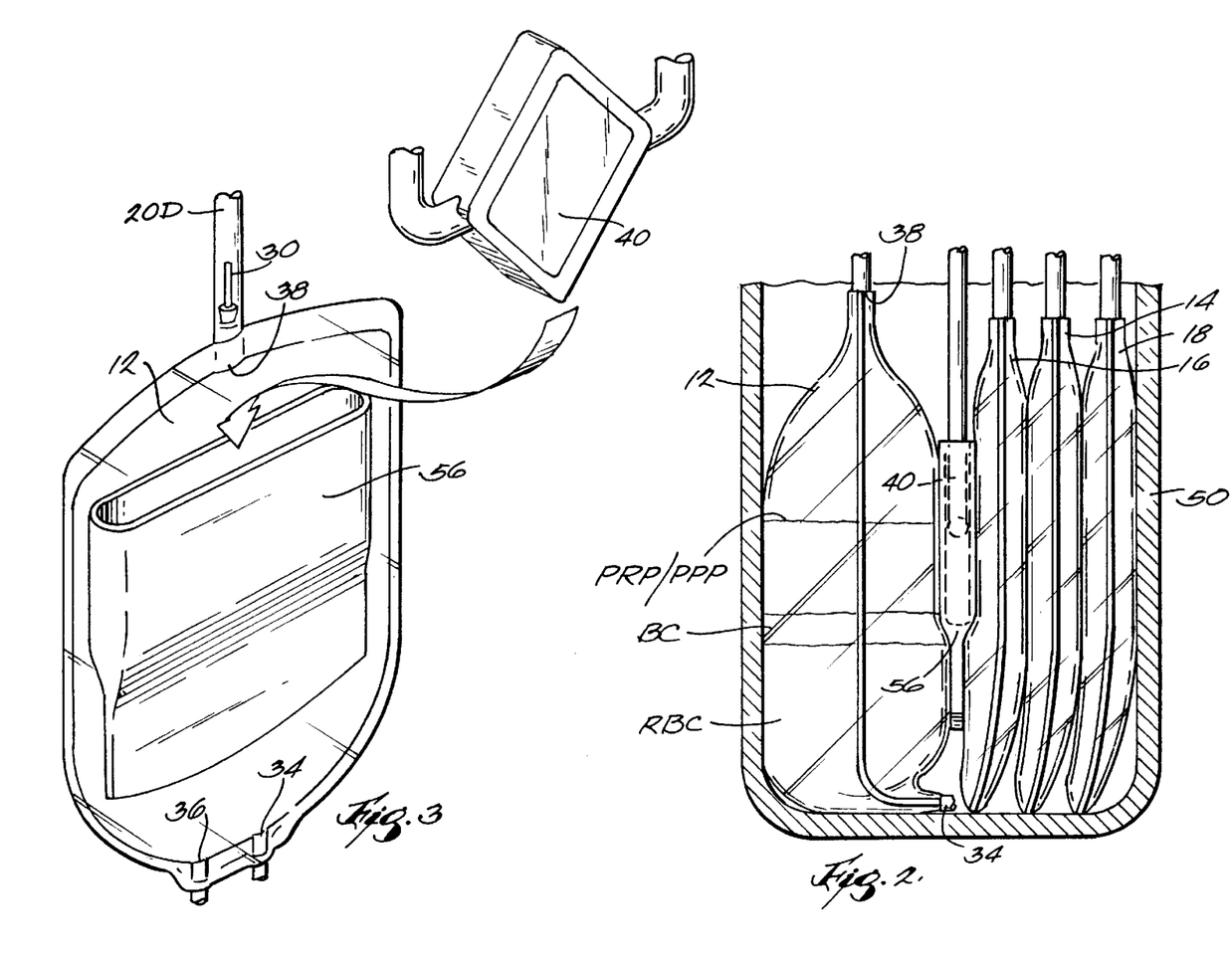
FIG. 2 is a side section view of the assembly shown in FIG. 1 when nested within a centrifuge bucket, showing the integral separation device retained within in a flexible protective pouch.
FIG. 3 is an exploded perspective view of the separation device and the flexible protective pouch, when nested against the primary bag, as would occur within the centrifuge bucket shown in FIG. 2.

The whole blood then undergoes separation by centrifugation within the primary bag 12. During this processing step (as FIG. 2 shows), the system 10 is placed as an integral assembly into a bucket 50 of a conventional blood centrifuge. The filter 40 remains integrally attached to the assembly 10 during the centrifugation process. As FIG. 2 shows, during centrifugation, the filter 40 occupies the blood centrifuge bucket 50 alongside the bags 12; 14; 16; and 18, which nest in succession one against the other. In this arrangement, the filter 40 is sandwiched within the bucket 50 next to the primary bag 18.

In the illustrated and preferred embodiment (see FIGS. 2 and 3), the filter 40 is housed within a flexible pouch 56 during centrifugation within the bucket 50. The pouch 56 creates a soft yet relatively stiff interface between the filter 40 and the adjacent bags 12; 14; 16; and 18 within the bucket. The pouch 56 shields the bags in the bucket 50 from direct contact against the filter 40 during centrifugation. In this way, the pouch protects the bags from puncture or damage during processing.

Further details of the pouch are disclosed in U.S. Patent application Ser. No. 08/077,288, filed Jun. 14, 1993, entitled "Closed Systems and Methods for Removing Undesired Matter from Blood Cells."

The bucket 50 is spun at high speeds to centrifugal separate the whole blood within the primary bag 16 into the red blood cell (RBC) component and PRP or PPP plasma component, as FIG. 2 shows.

Whether the separation process provides PRP or PPP plasma component depends upon the rotational speed and time of processing. Slower rotational speeds over a given time period (called a "soft" spin) produce PRP. Higher rotational speeds over the same time period (called a "hard" spin) yield fewer platelets in the plasma, produce PPP.

As FIG. 2 shows, during centrifugation, the heavier RBC component collects in the bottom of the primary bag 12. The lighter PRP/PPP plasma component collects at the top of the primary bag 12 during centrifugation.

During centrifugal separation, an intermediate layer of leukocytes (commonly called the "buffy coat" and identified as BC in FIG. 2) forms between the red blood cell component and the PRP/PPP plasma component. If the plasma component is PPP, the buffy coat also includes a substantial amount of platelets. If the plasma component is PRP, substantially fewer of platelets remain in the buffy coat.

Figure 4:
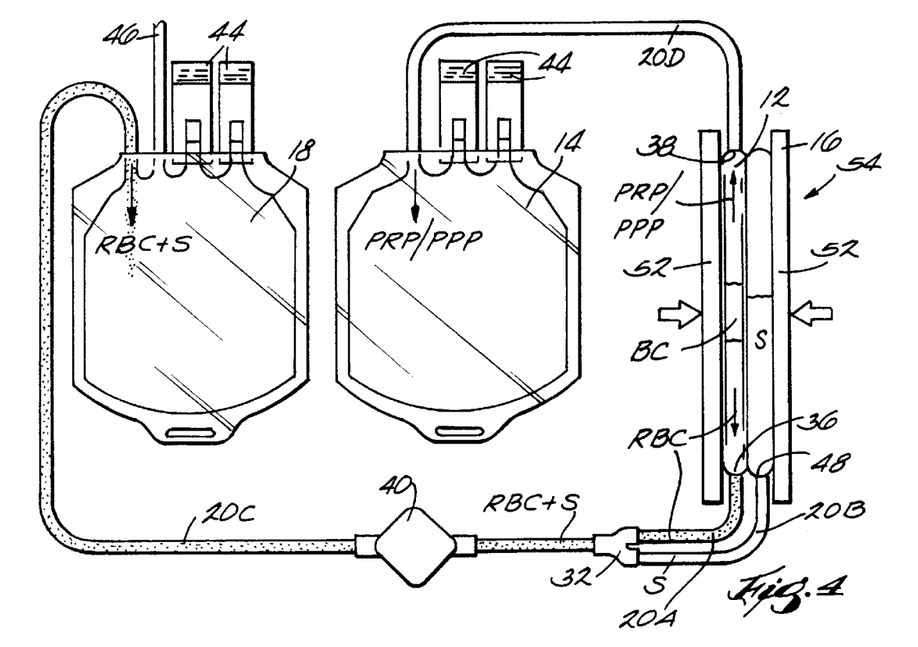
FIG. 4 is a schematic view of the assembly shown in FIG. 1 when used to transfer plasma component and RBC component to associated transfer bags, the RBC component being mixed with an additive solution and transferred through a separation device to remove undesired matter from the RBC component.

Following the centrifugation step, the user removes the system 10 from the centrifuge bucket 50. The user places the primary bag 12 and additive solution bag 16 between two spaced apart plates 52 of a fluid transfer system 54 (see FIGS. 4 and 6), which will be described in greater detail later.

The user manually breaks the cannulas 26; 28; and 30 open. The primary bag 12 and additive solution bag 16 are simultaneously compressed or squeezed between the two plates 52 (see FIG. 4). The compression expresses the PPR/PPP component from the top port 38 of the bag 12, through the tube branch 20D and into the transfer bag 14. The RBC component is also expressed by the same action from the bottom port 36 of the bag 12 into the tube branch 20A, just as the additive solution is also expressed from the bottom port 48 of the bag 16 into the tube branch 20B. The buffy coat layer BC remains behind in the bag 12.

Figure 6:
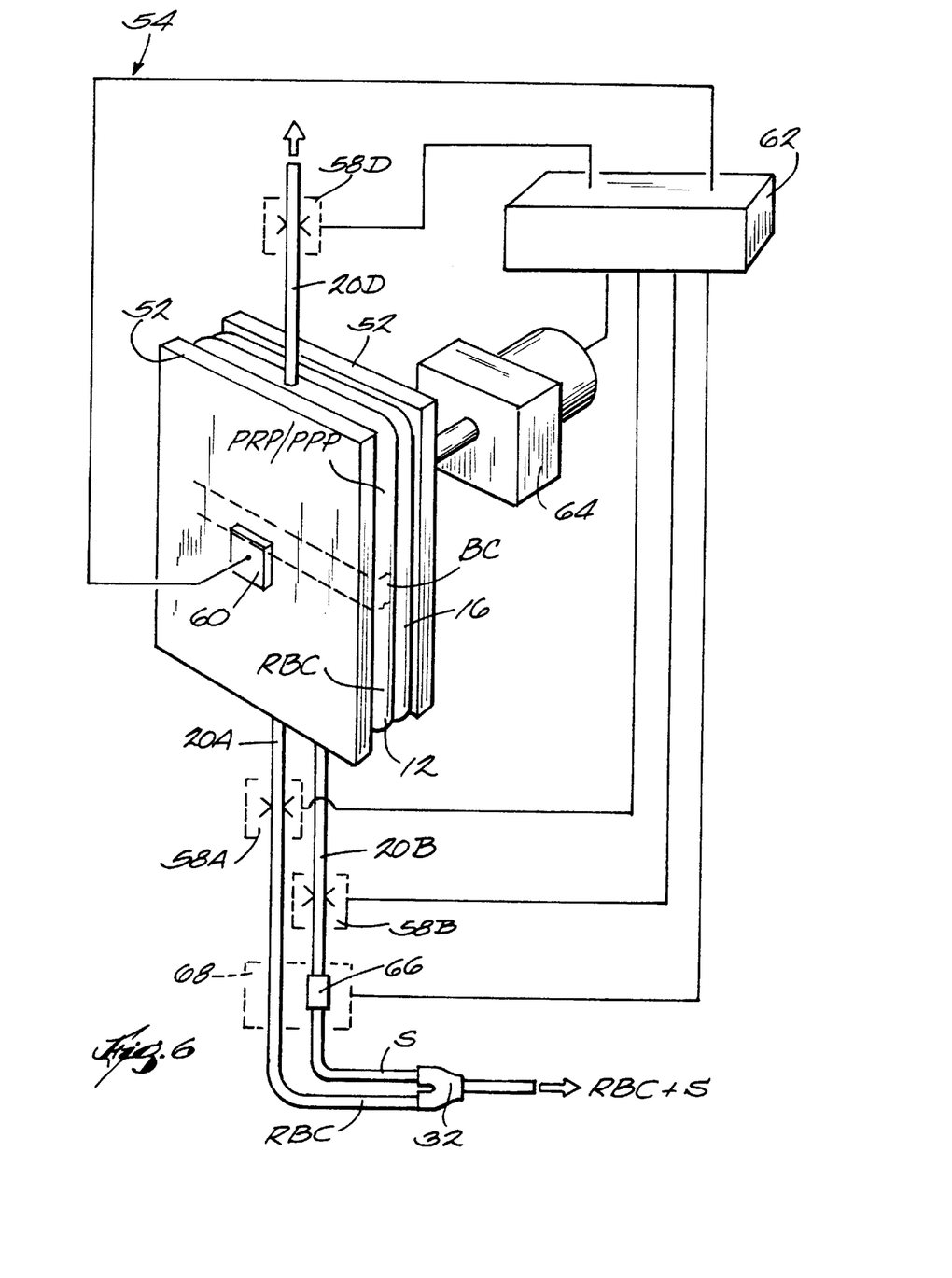
FIG. 6 is a largely diagrammatic view of the system used to expel selected blood components and additive solution from the assembly shown in FIG. 1.

As FIG. 6 shows, the system 54 includes electrically actuated solenoid clamps 58A, 58B, and 58D, which are operatively associated with the branch tubes 20A, 20B, and 20D, respectively. The system 54 also includes an optical sensing device 60, preferably carried by one of the plates 52 to sense the location of the interface between the RBC and BC in the bag 12 while being squeezed. A controller 62 is electrically coupled to the sensor 60, the clamps 58A/58B/58D, and to an actuator 64 for the plates 52. The controller 62 commands the actuator 64 to move one or both plates 52 to simultaneously squeeze the bags 12 and 16. The controller 62 also commands the clamps 58A/58B/58C to open and close to coordinate flow of PRP/PPP through the tube branch 22D; RBC through the tube branch 22A; and additive solution through the tube branch 22B.

Johansson et al U.S. Pat. No. 4,350,585 discloses further details of a device that compresses a primary blood collection bag to expel plasma and RBC components from the top and bottom ports. A commercial embodiment of such a device is sold by Baxter Healthcare Corporation (Fenwal Division) under the tradename OPTIPRESS.

Preferably, the controller 62 coordinates operation of the clamps 58A/58B/58D in response to signals generated by the sensor 60, to keep the buffy coat (BC) sandwiched between the PRP/PPP component and RBC component within the bag 12, while the plasma and red blood cell components are expressed from the primary bag 12. This preferred technique retains the buffy coat in the primary bag 12 and, with it, most of the leukocytes for subsequent harvesting or disposal. This technique provides from about 0.75 to about 1.00 reduction in the number of leukocytes in the PRP/PPP plasma component and RBC component, when compared to the leukocytes contained in the whole blood.

As FIG. 2 and 6 show, while the bag 12 and bag 16 are simultaneously squeezed by the plates 52, the PRP/PPP plasma component flows through the tube branch 20A into the transfer/storage bag 14. The RBC component likewise flows through the tube branch 20B and into tube branch 20C, where it mixes with the additive solution flowing through tube branch 20B also into tube branch 20C. The RBC component (mixed with storage solution S) then flows through the filter 40 into the transfer bag 18 by virtue of the compression force exerted by the plates 52.

The removal of leukocytes by the filter 40 supplements the previously described top-and-bottom port separation and compression process, which keeps substantial leukocytes in the bag 12 to begin with. Depending upon the characteristics of the filter 40, the use of the filter provides an additional 0.5 to about 1.0 log reduction, or more, in the number of leukocytes in the RBC component entering the transfer bag 18 for storage.

The rate of expression of the additive solution in tube branch 20B relative to the rate of expression of the RBC in tube branch 20A can be controlled in various ways. As FIG. 6 shows, a mechanical restrictor 66 can be placed in-line in the tube branch 20B to meter the flow of additive solution, thereby obtaining a desired ratio of RBC to additive solution. Alternatively, as shown in phantom lines in FIG. 6, an electronic monitoring and feedback device 68 can perform the same function under the control of the controller 62.

Figure 5:
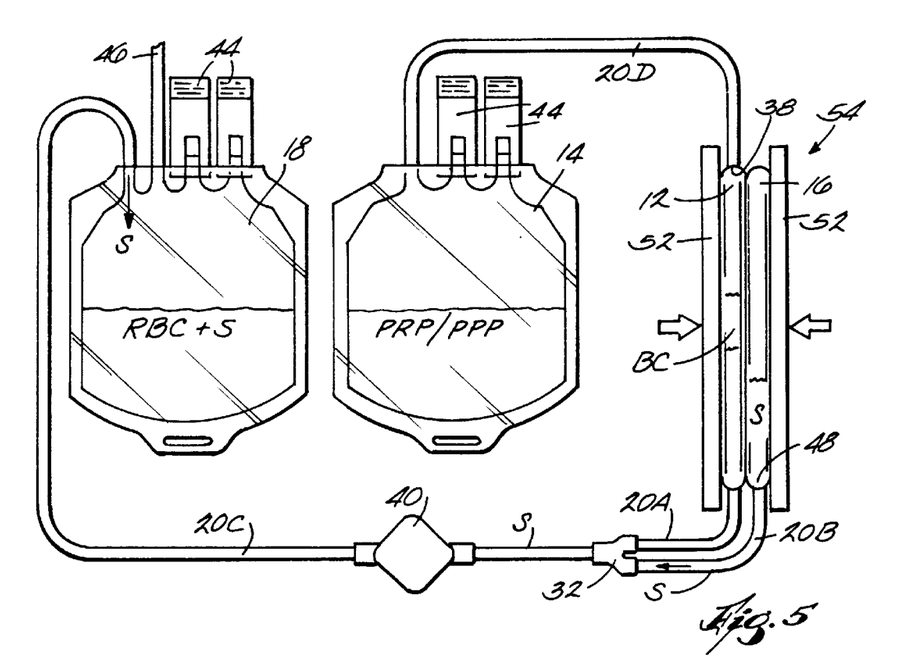
FIG. 5 is a schematic view of the assembly shown in FIG. 1, with the additive solution being used to flush RBC component from the separation device that removes undesired matter.

Once a desired volume of RBC has been expelled from the primary 12, the controller 62 commands the red blood cell clamp 58A to close. Preferably, the controller 62 commands the actuator 64 to apply pressure to the plates 52 for a predetermined time period, while leaving the additive solution clamp 58B open. In this way, the controller 62 expels an additional volume of additive solution from the bag 18 into the transfer bag 18, through the tube branch 20C and filter 40 (see FIG. 5). This additional volume of additive solution flushes trapped residual volume of RBC component from the filter 40 and tube branch 20C into the transfer/storage bag 18.

Once the desired volumes of plasma and red blood cell components are collected in the bags 14 and 18, the transfer bag 14 (containing the PRP/PPP component) and the transfer bag 16 (containing the leukocyte-depleted RBC component mixed with storage solution S) can be separated in a sterile fashion from the primary bag 12 (containing the BC component) for independent handling. A conventional heat sealing device (for example, the Hematron® dielectric sealer sold by Baxter Healthcare Corporation) can be used for this purpose.

Figures 7, 8:
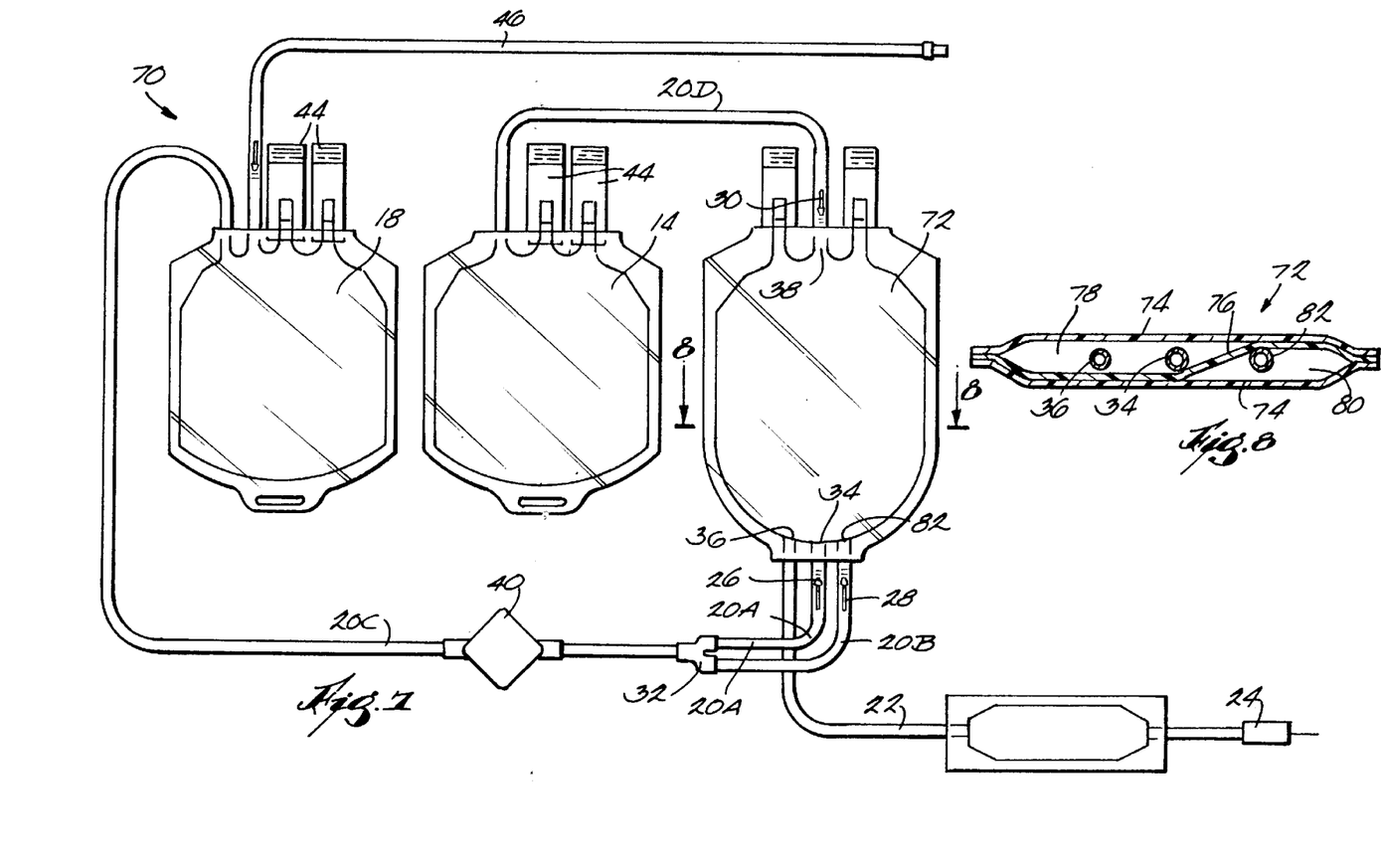
FIG. 7 is a schematic view of an alternative blood collection assembly that embodies the features of the invention with the inclusion of a double chamber primary bag.
FIG. 8 is an interior view of the double chamber primary bag taken generally along line 8—8 in FIG. 7.

FIGS. 7 and 8 show an alternative system 70 that embodies the features of the invention. The system 70 shown in FIGS. 7 and 8 is, in most respects, identical to the system 10 shown in FIG. 1. Common reference numerals are therefore used to identify common elements.

The system 70 includes a primary bag 72 with integral donor tube 22. Tube branches 20A/20C/20D couple the primary bag 72 to the transfer bags 14 and 18. The tube branch 20C also includes the in-line filter 40, just as the system 10 shown in FIG. 1.

Unlike the system 10 shown in FIG. 1, the system 70 shown in FIG. 7 does not include a separate bag 16 for the additive solution. Instead, the primary bag 72 comprises a double chamber container. As FIG. 8 shows, the bag 72 includes exterior side walls 74 and an interior wall 76 sealed at their peripheries to compartmentalize the bag 72 into first and second chambers 78 and 80. Bottom ports 34 and 36 of the bag 72 communicate with the first chamber 78 and with the tube branch 20A and the donor tubing 22, respectively. This chamber, in use, is intended to receive whole blood for centrifugal separation and processing, just as the bag 12 shown in FIG. 1. The chamber 78 therefore also contains an anticoagulant solution.

Unlike the bag 12 of FIG. 1, the bag 72 further includes a third bottom port 82. This port 82 communicates only with the second chamber 80 and the tube branch 20B. The second chamber 80 of the bag 72, in use, is intended to contain the additive solution, thereby eliminating the need for a separate dedicated auxiliary bag 16 shown in FIG. 1.

The system 70 is handled during processing just like the system 10 shown in FIG. 1, as already described. The system 70, containing whole blood in the first chamber 78 and additive solution in the second chamber 80, undergoes centrifugation as a integrated unit. Following centrifugation, the double chamber bag 72 is placed between the two plates 52 to simultaneously express RBC from the first chamber 78 and additive solution from the second chamber 80 for mixing in the tube branch 20C and filtration by the filter 40. The consolidation of the additive solution container and the blood collection container into a single bag 72 further simplifies handling.

Various modifications of the invention will be apparent to those skilled in the art within the purview of the following claims.

I claim:

1. A blood processing system comprising a first variable volume chamber to hold blood, a second variable volume chamber to hold additive solution for blood, a separation device to remove undesired material from blood, an actuated element comprising plates spaced apart to accommodate placement of both the first variable volume chamber and the second variable volume chamber between the plates and including means for moving the plates together to exert a squeezing force simultaneously upon both first and second variable volume chambers to simultaneously expel a first flow of blood from the first variable volume chamber and a second flow of additive solution from the second variable volume chamber, and a fluid flow system to convey fluid flow in response to the squeezing force exerted by the actuated element and without application of external pumping force, the fluid flow system including a first branch communicating with the first variable volume chamber to convey the first flow of blood, a second branch communicating with the second variable volume chamber to convey the second flow of additive solution simultaneously with and independent of the first flow, a third branch communicating with the first and second branches to mix outside the first and second variable volume chambers the blood from the first branch with the additive solution from the second branch to create a mixed flow comprising blood and additive solution, the third branch further communicating with the separation device to direct the mixed flow of blood and additive solution through the separation device.

2. A system according to claim 1 and further including a transfer chamber, and wherein the third branch also communicates with the transfer chamber to direct the mixed flow of blood and additive solution from the separation device into the transfer chamber.

3. A system according to claim 1 wherein the first and second variable volume chambers comprise, respectively, a first flexible container and a separate second flexible container.

4. A system according to claim 1 wherein the first and second variable volume chambers comprise compartments within a single flexible container.

5. A system according to claim 1 wherein the separation device removes leukocytes.

6. A system according to claim 1 wherein the separation device comprises a leukocyte filter.

* * * * *